United States Patent [19]

Drake et al.

[11] Patent Number: 4,634,794

[45] Date of Patent: Jan. 6, 1987

[54] PROCESS FOR THE PRODUCTION OF ALLYL ACETATE

[75] Inventors: Charles A. Drake; Stephen E. Reiter, both of Bartlesville, Okla.

[73] Assignee: Phillips Petroleum Co., Bartlesville, Okla.

[21] Appl. No.: 821,929

[22] Filed: Jan. 24, 1986

Related U.S. Application Data

[62] Division of Ser. No. 663,629, Oct. 22, 1984, Pat. No. 4,587,229.

[51] Int. Cl.$^4$ .............................................. C07C 67/05
[52] U.S. Cl. ..................................... 560/245; 560/243
[58] Field of Search ................................ 560/243, 245

[56] References Cited

U.S. PATENT DOCUMENTS

| | | | |
|---|---|---|---|
| 3,221,045 | 11/1965 | McKeon | 260/497 |
| 3,274,238 | 9/1966 | Kojer | 260/497 |
| 3,313,840 | 4/1967 | Kosel | 260/465.8 |
| 3,600,429 | 8/1971 | Kronig | 260/475 N |
| 3,670,014 | 6/1972 | Fernholz | 560/245 |
| 3,700,745 | 10/1972 | Kovach | 260/672 |
| 3,925,452 | 12/1975 | Swodenk | 260/497 |
| 3,939,199 | 2/1976 | Fernholz | 260/469 |
| 3,950,400 | 4/1976 | Fernholz | 260/497 |
| 3,960,930 | 6/1976 | Clark | 260/475 N |
| 3,965,152 | 6/1976 | Smith | 260/491 |
| 3,965,153 | 6/1976 | Smith | 260/491 |
| 3,965,154 | 6/1976 | Smith | 260/491 |
| 4,010,198 | 3/1977 | Roscher | 260/497 |
| 4,056,563 | 11/1977 | Boyadzhian | 560/245 |
| 4,133,962 | 1/1979 | Fernholz | 560/245 |
| 4,158,737 | 6/1979 | Bartsch | 560/245 |
| 4,192,777 | 3/1980 | McVicker | 252/447 |
| 4,409,396 | 10/1983 | Dempf | 560/245 |

*Primary Examiner*—Michael L. Shippen
*Attorney, Agent, or Firm*—Stephen E. Reiter

[57] ABSTRACT

A process and catalyst for the acetoxylation of propylene, said catalyst consisting essentially of palladium, bismuth, and rubidium on a support.

7 Claims, No Drawings

PROCESS FOR THE PRODUCTION OF ALLYL ACETATE

This application is a division of application Ser. No. 663,629, filed 10/22/84, now U.S. Pat. No. 4,587,229.

BACKGROUND

This invention relates to a process for the production of allyl acetate. More particularly the present invention relates to the production of allyl acetate by the acetoxylation of propylene.

It is known that allyl acetate can be produced by reacting propylene, oxygen, and acetic acid over a palladium-containing catalyst. Numerous examples of promoters for the catalyst are reported in the literature. One of the more effective types of catalysts are those comprising palladium, potassium, and bismuth supported on an inert support. Even with such catalysts the optimum conditions have been found to give only about 5–10% conversion of the propylene, with no more than about 90% selectivity to allyl acetate for a space time yield of about 250–320 grams of allyl acetate per liter of catalyst per hour.

Obviously, it would be desirable to have a process which provided still better selectivity, conversion, or space time yield.

An object of the present invention is to provide an improved process for the acetoxylation of propylene. Still another object of the present invention is to provide a composition of matter suitable for use as a acetoxylation catalyst.

SUMMARY OF THE INVENTION

In accordance with the present invention a process is provided for preparing allyl acetate comprising reacting propylene, acetic acid, water, and oxygen under suitable reaction conditions in the presence of a catalyst consisting essentially of palladium, bismuth, and a promoting amount of rubidium deposited on a support.

DETAILED DESCRIPTION

The catalysts of the present invention are prepared by depositing the active components on the support and subsequently drying the resulting composite.

The supports include those typically used for acetoxylation catalysts. Examples include silica, aluminum oxide, aluminum silicates, silicates, titanium oxide, zirconium oxide, titanates, pumice silicium carbide, silica gel, spinels, and mixtures thereof. It is preferred to use supports having a high chemical resistance to water and acetic acid such as silica for example. Especially suitable are silica having a nitrogen surface area in the range of 40 to 350 m$^2$/g.

The palladium of the catalyst can be in the form of free palladium metal or in the form of a compound of palladium which is preferably free of halogens, sulfur, and nitrogen. Examples of such compounds include palladium acetate, palladium propionate, palladium acetylacetonate or palladium hydroxide. It is currently preferred to employ a palladium carboxylate, especially palladium acetate.

The other active components are applied in the form of acetates or compounds which will be converted to acetate either during the catalyst prep or during the acetoxylation process. Examples include the formates, propionates, hydroxides, carbonates, phosphates, borates, citrates, tartrates, or lactates of the other active metal components.

The catalyst can be prepared in many different ways, for example a compound of the metal can be dissolved in a solvent, the support impregnated with the resulting solution and then dried. It is also possible, however, to impregnate the support successively with the components which can then be converted, if required, by an intermediate treatment, such as calcination, or chemical reactions such as for example treatment with solutions of an alkali metal hydroxide, alkali metal carbonate or a reducing agent. The catalysts can be prepared from a compound containing sulfur, nitrogen or halogen, which compound is then converted on the support into an insoluble compound which is substantially free of sulfur, nitrogen or halogen.

The currently preferred technique of preparing the catalyst, however, involves dissolving the metal components in glacial acetic acid, then impregnating the support, and then drying the resulting solid.

The amount of palladium employed on the catalyst can vary from about 1 to about 3 weight percent, most preferably about 1 to about 2 weight percent based on the weight of the support.

The amount of bismuth can vary from about 1 to about 3 weight percent, more preferably about 1.5 to 2.5 weight percent based on the weight of the support.

Typically, the amount of rubidium will be in the range of 0.5 weight percent to 2.5 weight percent, most preferably about 1.0 to 1.5 weight percent based on the weight of the support.

In carrying out the acetoxylation propylene, oxygen, and acetic acid in the gaseous phase are contacted with the inventive catalyst at a temperature in the range of about 100° C. to about 250° C. and pressures of 1 to 25 absolute atmospheres. It is advantageous to use a concentration ratio which ensures that the reaction mixture does not attain the known explosion limits. The simplest way to do this is to keep the concentration of oxygen low, e.g. about 3 to 8% of the total feed employed. Generally, the non-reacted products may be recycled in a cyclic process.

It has been typically noted that the preferred results are obtained if the reaction is carried out at a temperature in the range of about 160° C. to about 180° C. and a pressure of about 42 to 120 psig, more preferably 75 to 100 psig.

The reaction mixture may also contain diluent gas which does not adversely affect the reaction such as nitrogen, carbon dioxide, and saturated hydrocarbons.

The amount of water employed is generally in the range of about 10 to about 35 weight percent of the acetic acid, more preferably about 20 to 30 weight percent.

The rate of contact of reactants and catalyst can vary over a wide range depending upon the conditions employed. Typically, however, the aqueous acetic acid would be supplied at a rate of about 0.4 to about 1.2 volumes per volume of catalyst per hour, more preferably about 0.7 to 0.9. The propylene would typically be supplied at a rate sufficient to provide about 0.5 to about 2 grams of propylene per milliliter of catalyst per hour, more preferably about 0.7 to about 1.5 g/ml/hr.

A further understanding of the present invention and the advantages that it provides will be provided by the following examples.

In the following examples the general procedure involved in preparing the catalysts involved dissolving the metal salts is glacial acetic acid, immersing the support with the solution, soaking the support for 2 hours.

The pressure was 75 psig and the temperature was 170° C.

TABLE I

EFFECT OF CATALYST COMPONENT CONCENTRATIONS ON REACTION RESULTS

| Run No. | HOAc feed | Pd,[2] % | K,[2] % | Bi,[2] % | Rb,[2] % | Selectivity, % | Conversion, % | STY, g/l/hr |
|---|---|---|---|---|---|---|---|---|
| 1 | Neat | 1.5 | 4.8 | 2.0 | — | 88.7 | 12.0 | 176 |
| 2 | Neat | 1.5 | 4.8 | 2.0 | 1.2 | 91.2 | 23.6 | 357 |
| 3 | Aqueous | 1.5 | 4.8 | 2.0 | 1.2 | 82.0 | 18.2 | 241 |
| 4 | Neat | 1.5 | — | 2.0 | 1.2 | 74.4 | 6.2 | 121 |
| 5 | Aqueous | 1.5 | — | 2.0 | 1.2 | 99.7 | 15.3 | 254 |

FOOTNOTES:
[2]Weight percent of the metal based on the support

Then the liquid was removed using a rotary evaporator and the catalyst dried by heating for 3 hours in a convection oven at 120° C. The support employed was a silica sold by Davison Chemical Co. as high surface area silica number G-59 of 8-12 mesh. The acetoxylations were carried out in a metal pipe ½" by 20" packed with 50 ml of catalyst. Heat was supplied via a steam jacked around the pipe. After oxidation was established it was continued for about 3 hours and then a total sample of the reactor effluent was taken for 2 hours. The products were analyzed on a 5880 Hewlett Packard gas chromatograph using a ⅛"×36" Poropak Q column. The quantities of oxidation products were used to calculate conversion, selectivity and catalyst productivity using the following formulas:

propylene conversion =

$$\frac{\text{moles allyl acetate} + \frac{1}{3} \text{moles CO}_2 \times 100\%}{\text{moles propylene}}$$

$$\text{allyl acetate selectivity} = \frac{\text{moles allyl acetate} \times 100\%}{\text{moles allyl acetate} + \frac{1}{3} \text{moles CO}_2}$$

$$\text{catalyst productivity } (STY) = \frac{\text{wt allyl acetate}}{\text{liter of catalyst/hr}}$$

EXAMPLE I

A series of catalysts were prepared using the acetates of Pd, Bi, and optionally K and/or Rb. The results of the employment of those catalysts in the acetoxylation of propylene are summarized in Table I.

The feed rates were as follows:

| Propylene | 35 g/hr |
|---|---|
| Oxygen | 4.5 L./hr |
| Acetic Acid Feed (Neat or Aqueous*) | 42 ml/hr |

*25% water based on the weight of the glacial acetic acid.

A comparison of runs 1 and 2 reveals that when the catalyst contains Pd, K, and Bi and the feed comprises glacial acetic acid the best results are obtained if the catalyst also contains rubidium. Run 3 reveals that there is no advantage to using aqueous acetic acid when the catalyst consists essentially of Pd, K, Bi, and Rb. Run 4 reveals that a catalyst consisting essentially of Pd, Bi, and Rb does not produce particularly desirable results. However, run 5 shows that when that catalyst is used with aqueous acetic acid the results are quite superior to those obtained when the Pd/K/Bi/Rb catalyst is used with aqueous acetic acid feed. Accordingly, the present disclosure makes it clear that if one is using an aqueous acetic acid feed one can do as well if not better without the K.

What is claimed is:

1. A process for preparing allyl acetate comprising reacting propylene, acetic acid, water, and oxygen in the presence of a catalyst consisting essentially of metals on a support said metals consisting essentially of palladium, bismuth, and rubidium.

2. A process according to claim 1 wherein the catalyst contains 1 to 3 weight percent palladium, 1 to 3 weight percent bismuth, and 0.5 to 2.5 weight percent rubidium.

3. A process according to claim 2 wherein the amount of water employed is in the range of about 10 to about 35 weight percent of the weight of the acetic acid.

4. A process according to claim 3 wherein said support is silica.

5. A process according to claim 4 wherein said catalyst contains about 1.5 weight percent palladium, about 2 weight percent bismuth, and about 1 weight percent rubidium, based on the weight of the support.

6. A process according to claim 5 wherein said catalyst is prepared by impregnating said support with acetates of the metals and then drying the catalyst.

7. A process according to claim 6 wherein the reaction is carried out at a temperature in the range of 100° C. to 250° C. and a pressure of 42 to 120 psig.

* * * * *